United States Patent [19]

Mercier

[11] Patent Number: 5,202,460
[45] Date of Patent: Apr. 13, 1993

[54] TERPENE DERIVATIVES, THEIR PREPARATION AND THEIR USE

[75] Inventor: Claude Mercier, Lyons, France

[73] Assignee: Rhone Poulenc Sante, Antony, France

[21] Appl. No.: 805,894

[22] Filed: Dec. 12, 1991

Related U.S. Application Data

[62] Division of Ser. No. 543,115, Jun. 21, 1990, abandoned.

[30] Foreign Application Priority Data

Jun. 22, 1989 [FR] France ................................. 89 08319

[51] Int. Cl.$^5$ ...................... C07C 49/24; C07C 45/65; C07C 67/00
[52] U.S. Cl. .................................... 560/126; 568/391; 568/395
[58] Field of Search ............... 560/250, 126, 174, 262; 568/391, 392, 393, 395, 414, 415

[56] References Cited

U.S. PATENT DOCUMENTS

| | | | |
|---|---|---|---|
| 3,330,867 | 7/1967 | Saucy | 260/594 |
| 3,519,681 | 7/1970 | Saucy | 260/488 |
| 3,574,715 | 4/1971 | Marbet et al. | 260/488 |
| 3,946,054 | 3/1976 | Klaiber et al. | 560/174 X |
| 4,035,395 | 7/1977 | Stetter et al. | 560/174 X |
| 4,097,531 | 6/1978 | Bledsoe, Jr. et al. | 260/586 R |
| 4,260,551 | 4/1981 | Mishima et al. | 260/410 |
| 4,460,786 | 7/1984 | Morel | 560/126 |
| 4,701,282 | 10/1987 | Chan et al. | 560/126 X |
| 4,806,280 | 2/1989 | Mignani et al. | 260/408 |
| 4,906,414 | 3/1990 | Morel | 560/174 X |

FOREIGN PATENT DOCUMENTS

0082781  6/1983  European Pat. Off. .

*Primary Examiner*—Arthur C. Prescott
*Attorney, Agent, or Firm*—Finnegan, Henderson, Farabow, Garrett and Dunner

[57] ABSTRACT

Terpene derivatives of formula I, their preparation and their use. In formula I, R represents a hydrogen atom or an alkanoyl radical and R' represents a hydrogen atom or an aliphatic hydrocarbon radical.

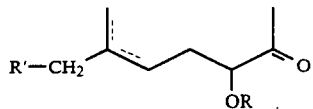

6 Claims, No Drawings

TERPENE DERIVATIVES, THEIR PREPARATION AND THEIR USE

This is a division of application Ser. No. 07/543,115, filed Jun. 21, 1990, now abandoned.

SUMMARY OF THE INVENTION

The present invention relates to new terpene derivatives of formula I:

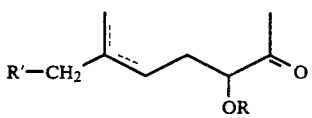

and to their preparation and use.

In formula I, R represents a hydrogen atom or an alkanoyl radical containing 1 to 4 carbon atoms, such as an acetyl radical, and R' represents a hydrogen atom or an aliphatic hydrocarbon radical containing 1 to 20 carbon atoms. Optionally, the aliphatic hydrocarbon has one or more double bonds, such as, a prenyl or geranyl radical.

Of very special interest are the terpene derivatives of formula I wherein R' represents a hydrogen atom or a prenyl radical ($CH_3C(CH_3)=CH-CH_2-$).

DETAILED DESCRIPTION OF THE INVENTION

A. According to the present invention, the new terpene derivatives of formula I, wherein R represents an alkanoyl radical, are obtained from an α-halo-β-keto ester of formula II:

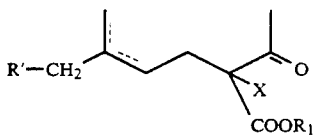

wherein R' is defined as above, X represents a halogen atom, preferably a chlorine atom, and $R_1$ represents an alkyl radical containing 1 to 4 carbon atoms, preferably a methyl or ethyl radical. The terpene derivatives of formula I are formed from the ester of formula II either by (1) acylation followed by decarboxylation, or (2) by decarboxylation followed by acylation of a compound of formula II.

In method (1), acylation is performed using a compound of formula II to obtain a compound of formula III:

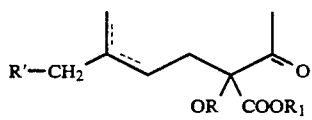

wherein R', R and $R_1$ are defined as above. Preferably, an alkali metal salt of an aliphatic acid of formula IV:

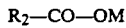

$R_2-CO-OM$    IV wherein $R_2$ represents a hydrogen atom or an alkyl radical containing 1 to 3 carbon atoms and M represents an alkali metal atom such as a sodium or potassium atom, is combined with a compound of formula II, in a polar organic solvent such as N-methylpyrrolidone, at a temperature of between about 50° C. and 200° C.

Decarboxylation is performed using a compound of formula III to obtain a compound of formula I by heating at a temperature of between about 20° C. and 200° C., preferably between about 50° C. and 100° C., in a polar organic solvent, such as N-methylpyrrolidone, in the presence of lithium chloride and a tertiary amine salt such as lutidine hydrochloride. This process is optionally prepared in situ.

In method (2), decarboxylation is performed using a compound of formula II to obtain a compound of formula V:

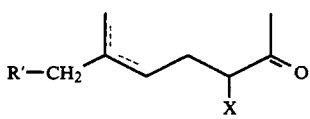

wherein R' and X are defined as above. This process is performed under the conditions described above for the decarboxylation of a compound of formula III to a compound of formula I.

Acylation of a compound of formula V to a compound of formula I is performed under the conditions described above for the acylation of a compound of formula II to a compound of formula III.

B. According to the present invention, the new terpene derivatives of formula I, wherein R represents a hydrogen atom are obtained by saponification of a compound of formula I wherein R represents an alkanoyl radical which is obtained as described above.

The saponification is preferably performed by means of a base, such as sodium hydroxide or potassium hydroxide, in an aqueous-alcoholic medium, such as a water/methanol mixture, at a temperature of between about 0° C. and 40° C.

The present invention relates to compounds of formula I, namely compounds of formula Ia and Ib:

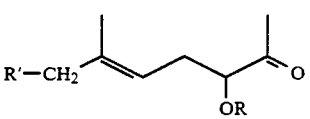

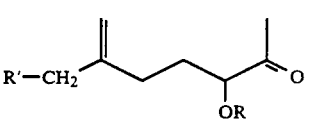

taken alone or in the form of a mixture.

Compounds of formula II are obtained by halogenation of a β-keto ester of formula VI:

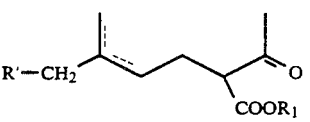

wherein R' and $R_1$ are defined as above, under the conditions described in European Patent EP 82,781.

Compounds of formula VI may be obtained by the action of an alkyl acetyl acetate on myrcene under the conditions described in European Patent EP 44,771. Compounds of formula V may also be obtained according to the processes described in U.S. Pat. Nos. 4,097,531 or 4,806,280.

The new terpene derivatives of formula I are especially useful intermediates in terpene synthesis. For example, compounds of formula I in which R represents a hydrogen atom or a prenyl radical are useful for preparing methylheptadienone or pseudoionone, which are especially important intermediates used in perfumery or in the synthesis of vitamin A. J. M. Defer et al., "Terpenoids", in Kirk-Othmer Encyclopedia 22, 709; H. Pommer et al., Pure and Appl. Chem. 43, 527 (1975).

For example, pseudoionone of formula:

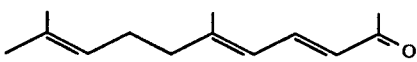

is obtained by pyrolysis of a compound of formula I wherein R' represents a prenyl radical and R represents an acetyl radical, or by dehydration, in the vapour phase over an acid catalyst (HOLDERICH, Angew. Chemie Int. Ed., 1988, 226) or in the liquid phase by means of phosphorus oxychloride, of a product of formula I in which R' represents a prenyl radical and R represents a hydrogen atom.

The examples which follow, given without implied limitation, show how the invention may be put into practice.

EXAMPLE 1

100 cc of N-Methylpyrrolidone and then 1.7 g (46.6 mmol) of gaseous hydrochloric acid were introduced under an argon atmosphere into a 250-cc three-necked round-bottomed flask. 1.36 g of anhydrous lithium chloride and 3.47 g (32 mmol) of 2,6-lutidine were added. The mixture was maintained at 25° C., and 5.36 g (17.4 mmol) of a 45:55 mixture of 3-chloro-3-carbomethoxy-6,10-dimethyl-5,9-undecadien-2-one and 3-chloro-3-carbomethoxy-10-methyl-6-methylene-9-undecen-2-one, having a purity of 98%, was added. Then the mixture was heated for 1 hour to 90° C. The mixture was extracted with a pentane/water mixture, and the organic phase was evaporated. 4.3 g of an oily orange-colored residue was obtained. The 3-chlorogeranylacetone content, determined by the proton nuclear magnetic resonance spectrum and by gas chromatography, was about 85%, and the degree of conversion was about 100%.

50 cc of N-methylpyrrolidone, 3.6 g (36.7 mmol) of potassium acetate; and 1.90 g of a portion of the product obtained above were introduced into a 100-cc three-necked flask. The mixture was heated for 1 hour to 88° C. under an argon atmosphere.

The mixture was extracted with a pentane/water mixture, and the organic phase was evaporated. A yellow oil was obtained, the analysis of which by thin-layer chromatography shows that the degree of conversion was about 100%.

The yellow oil was purified by flash chromatography, and then eluted with a pentane/ethyl acetate mixture. 1.6 g of a pale yellow oil was obtained consisting of a 40:60 mixture of 3-acetoxy-6,10-dimethyl-5,9-undecadien-2-one and 3-acetoxy-10-methyl-6-methylene-9-undecen-2-one, the structure of which was confirmed by the proton nuclear magnetic resonance spectrum, $^{13}C$ nuclear magnetic resonance spectrum, and infrared spectrum.

EXAMPLE 2

1.26 g (5 mmol) of 3-acetoxygeranylacetone in 20 cc methanol was introduced under an argon atmosphere into a 100-cc three-necked flask. 3.8 cc 38% (w/v) aqueous potassium hydroxide solution was added at 5° C. The mixture was stirred for 3 hours at 20° C. and then neutralized by the addition of hydrochloric acid.

The reaction mixture was extracted with pentane. After flash chromatography, 0.98 g of a colorless oil was isolated, the analysis of which, by the proton nuclear magnetic resonance spectrum, infrared spectrum and mass spectrum showed that was a 35:65 mixture of a compound of formulas:

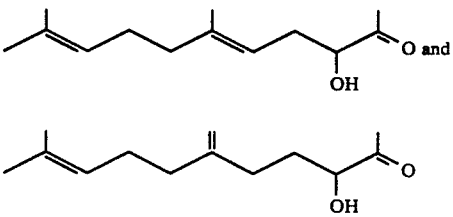

EXAMPLE 3

1.2 cc of pyridine and a 0.2 g (0.95 mmol) portion of the mixture of the compounds obtained in Example 2 was introduced into a 50-cc round-bottomed flask, and 0.1 cc phosphorus oxychloride was then added slowly at 0° C. Formation of a precipitate was observed. The mixture was neutralized and extracted with ether and then maintained for 2 hours at 0° C. 150 mg an orange-colored oil was obtained, of which the pseudoionone (EE+ZE) content was 80%. The structure of the product obtained was confirmed by the proton nuclear magnetic resonance spectrum, infrared spectrum and mass spectrum in comparison with an authentic sample. The degree of conversion was 100% and the yield of crude product was 66%.

I claim:
1. A process for preparing terpene derivatives of formula I:

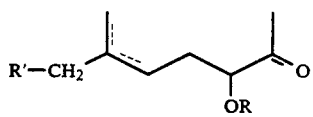

wherein R represents an alkanoyl radical containing 1 to 4 carbon atoms and R' represents a hydrogen atom or an aliphatic hydrocarbon radical containing 1 to 20 carbon atoms comprising:

a. acylating a compound of formula II:

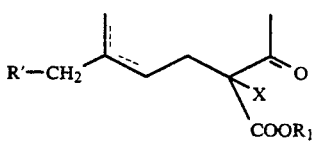

wherein R' is defined above, X represents a halogen atom and $R_1$ represents an alkyl radical containing 1 to 4 carbon atoms, by means of an alkali metal salt of an acid of formula IV:

$$R_2-CO-M \qquad IV$$

wherein $R_2$ represents a hydrogen atom or an alkyl radical containing 1 to 3 carbon atoms and M represents an alkali metal atom, to obtain a compound of formula III:

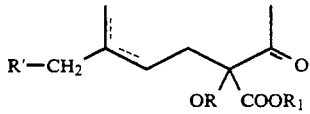

III wherein R' and $R_1$ are defined as above and R represents an alkanoyl radical containing 1 to 4 carbon atoms, and b. decarboxylating the compound of formula III to obtain a compound of formula I.

2. A process for preparing terpene derivatives according to claim 1, wherein M represents sodium or potassium.

3. A process for preparing terpene derivatives according to claim 1, wherein X represents chlorine.

4. A process for preparing terpene derivatives according to claim 1, wherein $R_1$ represents a methyl or ethyl radical.

5. A process for preparing terpene derivatives according to claim 1, wherein the acylation is performed in a polar organic solvent at a temperature of between about 50° C. and 200° C.

6. A process for preparing terpene derivatives according to claim 1, wherein the decarboxylation is performed in a polar organic solvent at a temperature of between about 20° C. and 200° C., in the presence of lithium chloride and a tertiary amine salt.

* * * * *